United States Patent
Bernard

(10) Patent No.: US 10,535,167 B2
(45) Date of Patent: Jan. 14, 2020

(54) METHOD AND SYSTEM FOR TOMOSYNTHESIS PROJECTION IMAGE ENHANCEMENT AND REVIEW

(71) Applicant: GENERAL ELECTRIC COMPANY, Schenectady, NY (US)

(72) Inventor: Sylvain Bernard, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/154,275

(22) Filed: Oct. 8, 2018

(65) Prior Publication Data
US 2019/0051023 A1    Feb. 14, 2019

Related U.S. Application Data

(63) Continuation-in-part of application No. 14/984,846, filed on Dec. 30, 2015, now Pat. No. 10,092,262.

(30) Foreign Application Priority Data

Dec. 31, 2014    (GB) .................................. 1423370.4

(51) Int. Cl.
| | | |
|---|---|---|
| *G06T 11/00* | (2006.01) | |
| *A61B 6/02* | (2006.01) | |
| *G06T 7/00* | (2017.01) | |

(52) U.S. Cl.
CPC ............ *G06T 11/005* (2013.01); *A61B 6/025* (2013.01); *G06T 7/0012* (2013.01); *G06T 2207/10116* (2013.01); *G06T 2211/436* (2013.01)

(58) Field of Classification Search
CPC combination set(s) only.
See application file for complete search history.

(56) References Cited

U.S. PATENT DOCUMENTS

| | | |
|---|---|---|
| 4,903,204 A | 2/1990 | Dobbins, III |
| 7,760,924 B2 | 7/2010 | Ruth et al. |
| 8,126,226 B2 | 2/2012 | Bernard et al. |
| 8,824,761 B2 | 9/2014 | Palma et al. |
| 9,842,415 B2 | 12/2017 | Bernard et al. |
| 10,092,262 B2* | 10/2018 | Bernard ............... A61B 6/5205 |
| 2007/0116343 A1 | 5/2007 | Sauer et al. |
| 2007/0183564 A1 | 8/2007 | Li et al. |
| 2011/0150178 A1* | 6/2011 | Bernard ................ G06T 11/008 |
| | | 378/22 |

FOREIGN PATENT DOCUMENTS

| | | |
|---|---|---|
| GB | 2453177 A1 | 4/2009 |
| WO | 2015054518 A1 | 4/2015 |

OTHER PUBLICATIONS

Combined Search and Exam Report for corresponding GB Appln. No. 1423370.4, dated Jul. 1, 2015, 5 pages.

* cited by examiner

*Primary Examiner* — Kim Y Vu
*Assistant Examiner* — Molly Delaney
(74) *Attorney, Agent, or Firm* — Fletcher Yoder, P.C.

(57) ABSTRACT

A method and system for obtaining images of an object of interest using a system comprising an X-ray source facing a detector. The method and system enable the acquiring of a plurality of 2D projection images of the object of interest in a plurality of orientations. A selected 2D projection image such as the zero projection of the plurality of projections can be enhanced by using at least a subset of the plurality of tomosynthesis projection images. The obtained enhanced 2D projection image is displayed for review.

14 Claims, 6 Drawing Sheets

METHOD AND SYSTEM FOR TOMOSYNTHESIS PROJECTION IMAGE ENHANCEMENT AND REVIEW

CROSS-REFERENCE TO RELATED APPLICATIONS

This application is a continuation-in-part of U.S. patent application Ser. No. 14/984,846, filed on Dec. 30, 2015, which claims priority to Great Britain Application No. 1423370.4, filed Dec. 31, 2014, now Great Britain Patent No. 2533801B, both of which are incorporated herein by reference in their respective entireties.

BACKGROUND

The present disclosure relates to the field of tomosynthesis imaging and to a method and system for processing tomosynthesis imaging data for obtaining enhanced projection images.

X-ray imaging systems have become a valuable tool in medical applications such as for the diagnosis of many diseases. As standard screening for breast cancer mammography two-dimensional (2D) X-ray images are taken across the entire breast tissue. These 2D mammograms are limited by tissue superimposition. That is to say, lesions may be hidden or masked by the tissue above or below, or normal structures may mimic a lesion. In order to minimize limitations of standard 2D mammography caused by tissue superimposition, digital breast tomosynthesis (DBT) using digital detectors has been developed.

The tomosynthesis imaging systems employ at least one X-ray tube, which is moved in an arc above a stationary detector. In digital breast tomosynthesis (DBT) the volume information of an object of interest can be derived from a series of images, known as projection images or projections, which are taken at various angles by means of one or more X-ray sources. Objects of different heights in a breast display differently in the different projections. From the 2D projection images, three-dimensional (3D) volume images can be generated for review. These generated 3D volume images offer advantages to overcome the limitations associated with tissue superimposition.

During the adaption period of tomosynthesis imaging technology, the availability of 2D mammography is still desired by medical professionals and radiologists, who want to use existing expertise gained from reviewing 2D mammograms. Furthermore, archived 2D mammograms can be better compared with images obtained with the same technology than with images of a new technology, such as tomosynthesis imaging technology.

To address the need for 2D mammograms besides the availability of the relatively recently available tomosynthesis images, it is known to perform a combo acquisition of 2D images and tomosynthesis images. That is to say both 2D mammograms and DBT images are acquired for the same object of interest. However, since the average dose from tomosynthesis imaging is approximately the same as 2D mammography imaging, the radiation exposure is roughly doubled. Thus, there is the need, to generate or acquire the information of 2D mammograms without performing two image acquisitions requiring two X-ray exposures, in order to reduce X-ray dose.

One problem to be addressed is that images acquired during DBT with the use of digital detectors may be contaminated by a variety of noise sources. By noise we refer to stochastic variations as opposed to deterministic distortions such as lack of focus. One drawback is that a single tomosynthesis projection image at a given orientation or X-ray source position is very noisy because the dose per projection is not enough to be compared to a 2D mammogram acquisition. Accordingly, there is a need to improve image quality comprising noise management in order to offer a tomosynthesis 2D image that looks like a 2D mammogram in order to enable high-quality diagnostic images.

Further, there is the need to facilitate lesion identification by a health professional by providing further imaging technologies, wherein not only one 2D image but also one or more 3D images are provided. This addresses the need for possible navigation and smooth transition from 2D to 3D images.

SUMMARY

In one aspect, the present disclosure is directed to a method for obtaining at least one enhanced image of an object of interest using a system comprising an X-ray source facing an X-ray detector. The method comprises acquiring a plurality of 2D tomosynthesis projection images of the object of interest in a plurality of orientations; enhancing a selected projection image of the plurality of projection images using at least a subset of the plurality of tomosynthesis projection images; and displaying the enhanced 2D projection image. The enhanced 2D projection image provides an overview of the object of interest such that a health professional or radiologist can review a patient's breast in one viewing.

According to an embodiment of the disclosure the enhancing step further comprises, for each pixel (i, j) of the selected projection image and for a given height accumulating the values of the corresponding pixel position in at least one of the tomosynthesis projections, ranking the accumulated values for each pixel over all possible heights; determining the most likely height for each pixel (i, j) by selecting the maximum accumulated value; and combining (i, j)'s level with the determined maximum values for each pixel (i, j).

The determined maximum values correspond to maximum accumulated values. The gray level of pixel (i, j) or (i, j)'s gray level corresponds to (i, j)'s gray level intensity value in the image. The accumulation process for each pixel (i, j) of the selected projection image can be a summation, averaging or any non-linear combination. In a particular embodiment, one can average the gray values among all the projections excluding the most contrasting value. By excluding the most contrasting value, artifacts introduced by highly contrasted objects are reduced.

In another aspect, the method step of accumulating is performed for different frequency bands obtained by filtering the projection images. In this way the different sizes of objects such as calcifications, fibers, masses and glands may be taken into account. By filtering, undesired artifacts can be avoided.

According to another embodiment the most likely height of each pixel (i, j) is stored as a height map associated to the enhanced 2D projection image.

According to yet another embodiment of the disclosure the most likely height of each pixel (i, j) is obtained as a combination of maximum accumulated value and 3D marks provided by a computer-aided diagnosis (CAD) system or indicated by a user through a 3D review system. In another embodiment, the method receives 3D findings locations as input. When pixel (i, j) is part of at least one finding's projection (the projection being performed on the image to be enhanced), the height associated to (i, j) becomes the finding's height. The height map is then modified accordingly. The value to be combined with the original (i, j)'s level becomes the accumulated value for the finding's height.

According to another embodiment of the disclosure the selected projection image is the central projection (0°), which is the projection perpendicular to or closest to the perpendicular of the detector. The central projection has advantageously the same geometry as a 2D mammogram. In case the object of interest is a patient's breast a 2D breast overview comparable to a 2D mammogram is provided.

In yet another aspect of the disclosure at least one tomosynthesis projection image is denoised prior to improving the image quality of at least one of the at least one tomosynthesis projection image. By way of example, directional filtering can be applied as one denoising method.

In another aspect, the method according to the disclosure further comprises enhancing the tomosynthesis projection images for each of the plurality of orientations; projecting each enhanced image on an isocentric virtual detector, wherein the normal to the virtual detector points towards the source position; and displaying successively the virtual projections.

Advantageously, the successive display provides an improved rendering effect wherein the user can quickly appreciate the breast content looking at different angulations. Preferably, the successive display is performed with an adjustable speed.

In another aspect, the present disclosure is directed to a computer program product, wherein the computer program product comprises program instructions for carrying out each of the method steps of the disclosure, when the product is executed on a computer.

In yet another aspect, the present disclosure is directed to a computer readable medium storing program instructions, which, when executed by a processor of a computer cause the computer to perform each of the method steps of the disclosure. In general, a computer-readable medium may be, for example, a hard disk, a CD-ROM, diskette, a ROM/RAM memory, DVD, a digital source such as a network or the internet or any other suitable means.

In yet another aspect, the disclosure is directed to a system for obtaining enhanced images of an object of interest. The system comprises an imaging system comprising an X-ray source and a detector configured to acquire a plurality of 2D tomosynthesis projection images of the object of interest such as a patient's breast; a processing unit configured to compute for a selected projection image of the plurality of projection images an enhancement using at least a subset of the plurality of projections; and a display unit configured to display the enhanced projection image.

At least one of the above embodiments provides one or more solutions to the problems and disadvantages of the background art. One technical effect that may be realized in the practice of all or some embodiments of the described methods and systems is to reduce radiation dose and improve at the same time dataflow and workflow efficiencies. Other technical advantages of the present disclosure will be readily apparent to one skilled in the art from the following description and claims. Various embodiments of the present application obtain only a subset of the advantages set forth. No single advantage is critical to the embodiments. Any claimed embodiment may be technically combined with any other claimed embodiments.

BRIEF DESCRIPTION OF THE DRAWINGS

The accompanying drawings illustrate exemplary embodiments of the disclosure and serve to explain, by way of example, the principles of the disclosure.

DETAILED DESCRIPTION

Radiologists would like to review 2D images acquired during a tomosynthesis acquisition. However, because the projections are of a low dose, their clinical content is limited. The method and system of the disclosure provides for improving the image quality of at least one tomosynthesis projection image using information or data from all of the other tomosynthesis projection images. The enhanced projections are then displayed sequentially as if acquired with an isocentric geometry leading to a 3D rendering.

The enhanced 2D tomosynthesis projection image provides a breast overview image that radiologists are used to looking at, a mapping of the lesions, and facilitates comparison to prior 2D images. If applied to all the tomosynthesis projection images and displayed sequentially, it may also help with motion detection. In addition, if projected on an isocentric virtual detector, it might give a 3D rendering sensation allowing for a rapid overview of the volume content.

Figure 1:
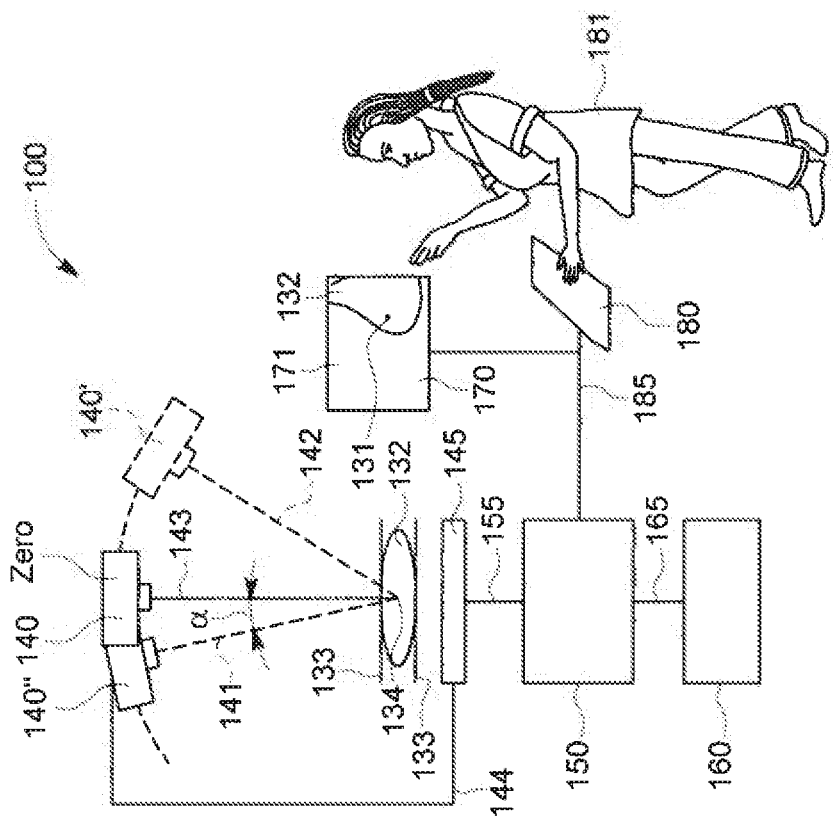
FIG. 1 is a diagrammatic illustration of an imaging system according to an exemplary embodiment of the disclosure.
Figure 1:
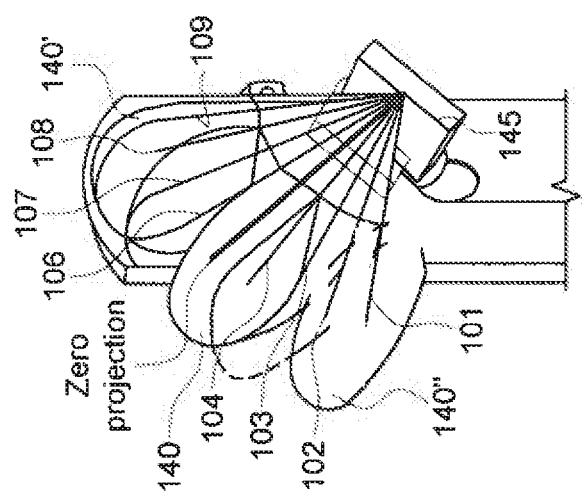

FIG. 1 is a diagrammatic illustration of an imaging system 100 for obtaining an enhanced projection image of an object of interest, wherein the system 100 comprises a X-ray source 140 facing an X-ray detector 145. The X-ray source 140 and the X-ray detector 145 are connected by an arm 144. Between the X-ray detector 145 and the X-ray source 140 an object of interest 132 can be placed. In the system illustrated, the X-ray source 140 moves in an arc above the X-ray detector 145. The X-ray detector 145 and a plurality of positions of the X-ray source 140' and 140" following an arc (see dashed line) are shown with dashed/solid lines and in a perspective partial view. In the shown arrangement, the X-ray detector 145 is fixed at the shown position and only the X-ray source 140 moves. However, in other embodiments, the X-ray detector 145 may move as well, such that the X-ray detector 145 follows the movement of the X-ray source 140 and is substantially perpendicular to the orientations 141, 142 and 143. The angle $\alpha$ is a projection angle enclosed by the zero-orientation and any other orientation such as 141 and 142. In this way multiple different views of the breast tissue can be acquired via the at least one X-ray source 140. The projection of lowest $\alpha$ or the projection closest to the zero-orientation is named the central projection or zero projection by approximation.

Still referring to FIG. 1, on the left side is shown a partial perspective view of an imaging system according to an exemplary embodiment of the disclosure comprising an X-ray detector 145 and an X-ray source 140. The different positions of the X-ray source 140, 140' and 140" are broadly depicted to illustrate the movement of the X-ray source. There are nine different projection views 101, 102, 102, 103, 104, 106, 107, 108, 109 including the zero projection (105) indicated as straight lines, which all point to the center of the X-ray detector 145.

The patient (not shown) is positioned in front of a mammography imaging system. To take for example, a mediolateral oblique (MLO) acquisition or view, a user or healthcare professional, such as a mammography technologist 181 will set the angle for the desired projection (30 degrees to 60 degrees, wherein 45 degrees represents the preferred zero projection shown in the perspective view of FIG. 1). During routine screening mammography, the angled MLO view is preferred over a lateral 90-degree projection because more of the breast tissue can be imaged.

The object of interest 132 shown in display unit 170 is a breast compressed by compression paddles 133, which ensure uniform compression and immobilization of the breast during the radiation exposure for optimal image quality. The breast 132 may include, for example, a calcification or lesion 131, which is located in the zero orientation 143, which is perpendicular to the detector 145 plane. The user may review calcifications, lesions or other clinically relevant structures for diagnosis. The display unit 170 may show a 2D mammography image, where mainly the middle portion of the breast 132 can be reviewed.

The X-ray detector 145 and the X-ray source 140 comprise an acquisition unit, which is connected via a data acquisition line 155 to a processing unit 150. The processing unit 150 comprises a memory unit 160, which may be connected to the processing unit 150 via an archive line 165.

The user or healthcare professional, such as the mammography technologist 181 may input control signals via a user interface 180. Such control signals are transferred from the user interface to the processing unit 150 via a signal line 185. The method and system according to the disclosure enables the user to obtain an enhanced 2D projection image that looks like a 2D mammogram. Based on this high-quality image, a radiologist is capable of identifying all the clinical signs relevant for breast screening. Especially if the user or healthcare professional is used to 2D mammograms, the user may easily analyze the displayed image. Further there is the possibility of displaying previously acquired 2D mammograms for comparison with an image acquired through a tomosynthesis imaging system according to the present disclosure. Besides, tomosynthesis images may be reviewed and archived. A CAD system or the user can provide 3D marks on images. A height map of clinically relevant structures or other objects obtained according to an embodiment of the disclosure can be combined with height information provided by 3D marks by a CAD system or indicated by a user through a 3D review system.

The memory unit 150 can be integral to or separate from the processing unit 150. The memory unit 160 allows storage of image data such as 2D enhanced projection images and tomosynthesis 3D images. In general, the memory unit 160 may comprise a computer-readable medium for example a hard disk or a CD-ROM, diskette, a ROM/RAM memory, DVD, a digital source such as a network or the Internet or any other suitable means. The processing unit 150 is configured to execute program instructions stored in the memory unit 160, which cause the computer to perform the methods of the disclosure. One technical effect of performing the method according to the embodiments of the invention is that the X-ray source may be less used, since the enhanced 2D projection images can replace a 2D mammogram, which usually is based on a separate X-ray exposure in order to acquire high-quality images.

Figure 2:
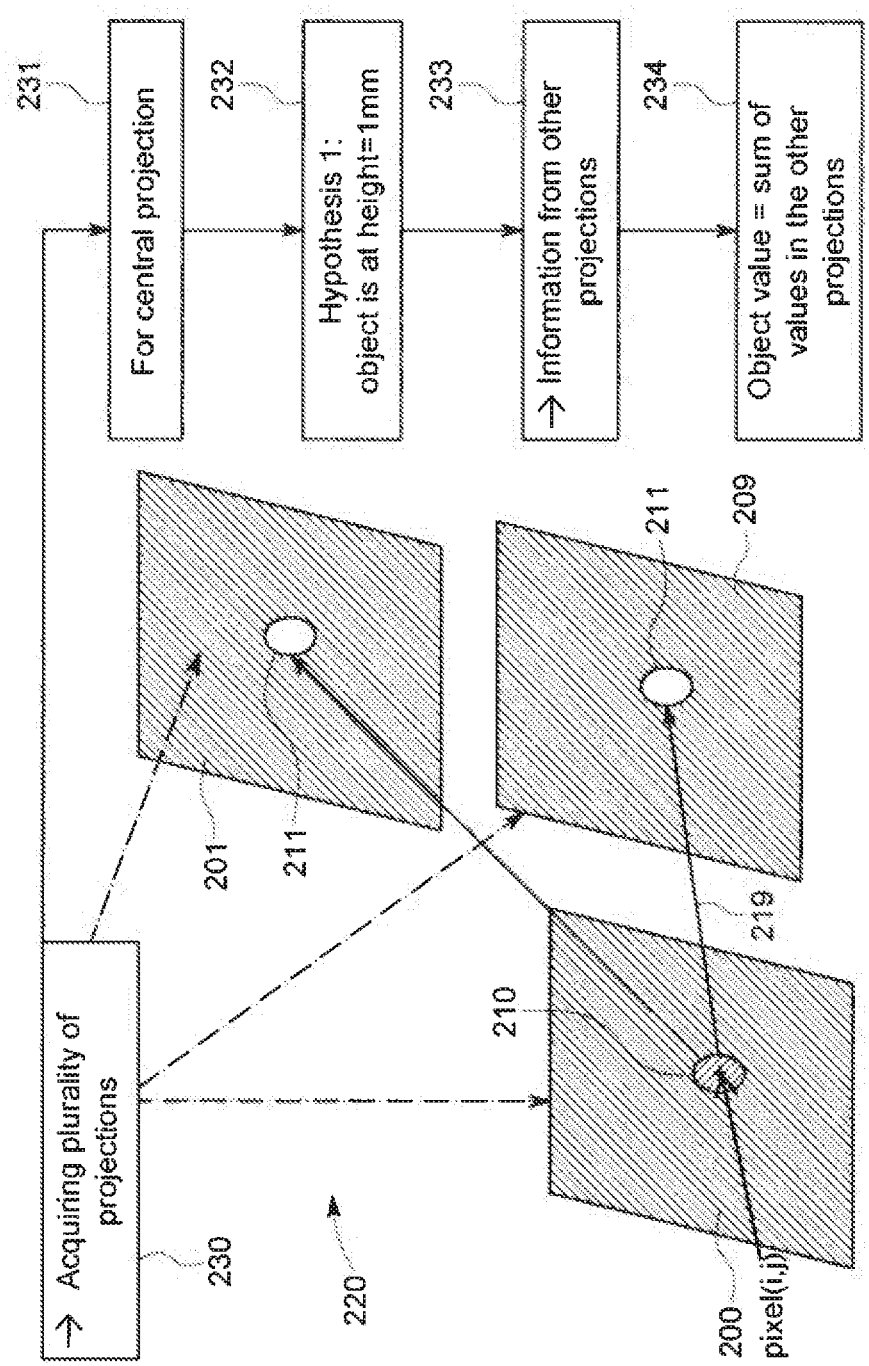
FIG. 2 is a diagrammatic illustration and flow chart of a method according to an exemplary embodiment of the disclosure for obtaining at least one enhanced image of an object of interest.

FIG. 2 illustrates schematically a method 220 according to an embodiment of the disclosure. In a first step, a plurality of 2D projection images are acquired. For example, nine (9) projections may be acquired in step 230. In order to generate an enhanced 2D projection image a central projection image is selected in step 231, since this central projection image has the same geometry and data content as a 2D mammogram. This central projection advantageously provides the underlying breast content.

However, all projection images are acquired at a low dose, which is many times lower than the dose needed for a 2D mammogram. This low dose results in low image quality, which needs to be improved or enhanced. In the central projection image, a 3D object 210 is a 2D representation of the 3D object 210 including pixel (i, j). The pixel (i, j) is indicated with the cross in the center of the 3D object 210. Due to the 2D representation of the 3D object 210, the height location of the 3D object within the volume of the breast is not known. The term "height" in this instance shall mean a given altitude or distance of an object in the breast volume relative to or spaced away from the X-ray detector. Since the height of the 3D object 210 is not known, the height is guessed or estimated in step 232. As a first hypothesis or starting point, a location of the 3D object is assumed to be at the height of 1 mm. Based on this first hypothesis, at least a subset of the plurality of other projection images are retrieved in step 233. This subset of other projection images are illustrated schematically by projection images 201-209. In step 234, the 3D object gray level intensity value is calculated by accumulating the gray level intensity values of 3D objects 211 found at the height of 1 mm in the other projection images.

Figure 3:
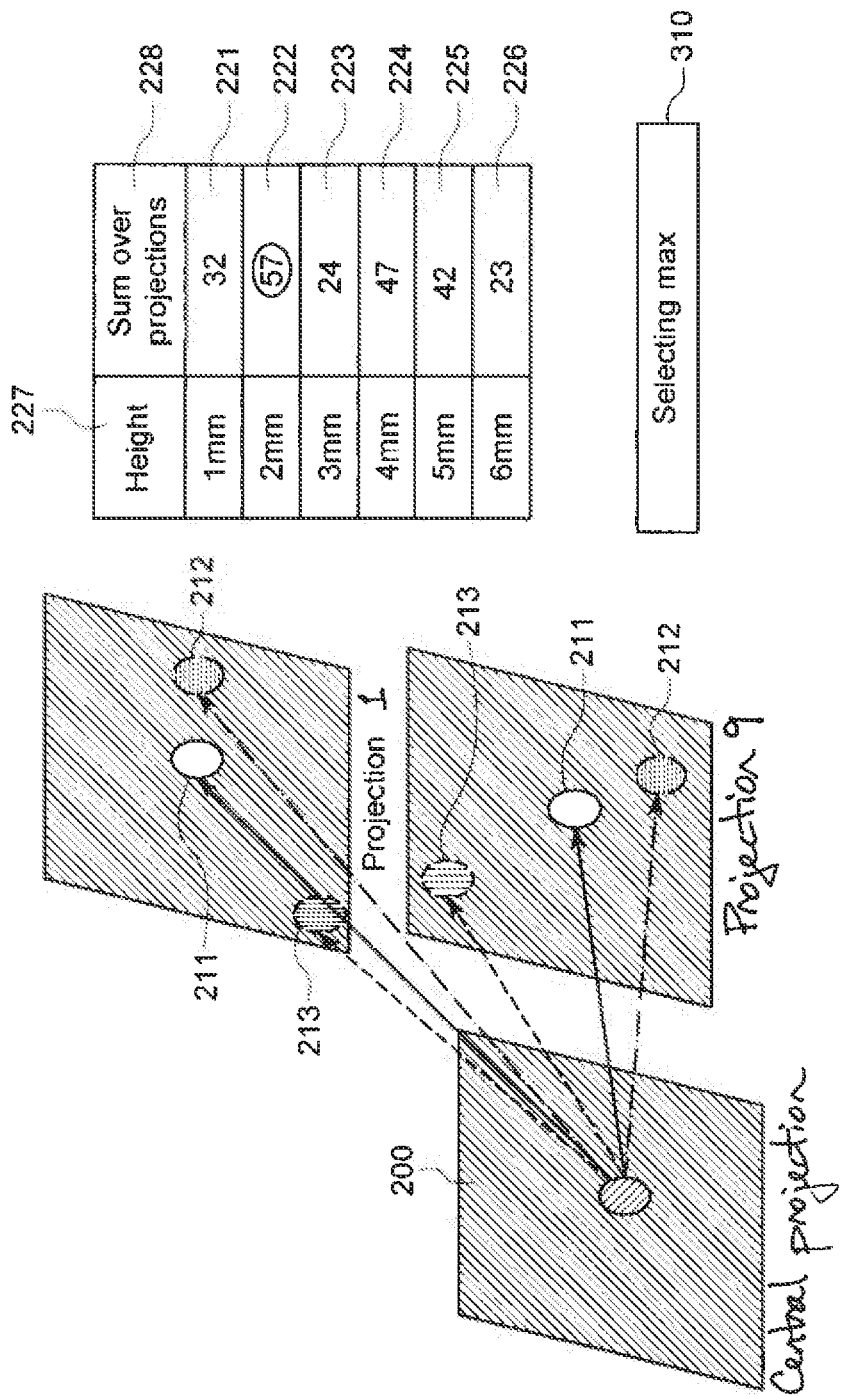
FIG. 3 is a diagrammatic illustration of a method according to another exemplary embodiment of the disclosure.

FIG. 3 shows the last step 234 described in FIG. 2 summarized in a height table. Similar to the first hypothesis, additional hypotheses are made for other heights in 1 mm steps or increments (e.g., 1 mm, 2 mm, 3 mm, etc.). The result of each hypothesis at a given height is depicted in the first column 227 comprising different height values and in the second column 228, which lists the sums of gray level intensity values in the other projections (221, 222, 223, 224, 225, 226). This method is schematically shown by the arrows originating from a 3D object or pixel (i, j) and pointing to the corresponding values in the other projections (201-209). The sums are then derived from the gray level intensity values of 3D objects 211, 212, 213 and corresponding pixel positions in the other projections.

In step 310, a maximum gray level intensity value is selected from the accumulated gray level intensity values. That is to say by ranking the accumulated gray level intensity values for each pixel over all possible heights, the most likely height for each pixel (i, j) can be determined. In this context, the term "most likely height" shall mean the estimated or most probable height for each pixel (i, j). Since the method to obtain the most likely height is an estimation method, the resulting height is with very high probability the actual height of the 3D object within the breast. In the illustrated example, a maximum gray level intensity value of 57 was determined at a height of 2 mm, such that the object is most likely positioned at this height. From this information of the most likely heights of each pixel (i, j), a height map can be generated. This height map can be associated with the enhanced 2D projection image. The enhanced 2D projection image is obtained by combining the gray level intensity values of pixel (i, j) with the determined maximum gray level intensity values for each pixel (i, j).

Figure 4:
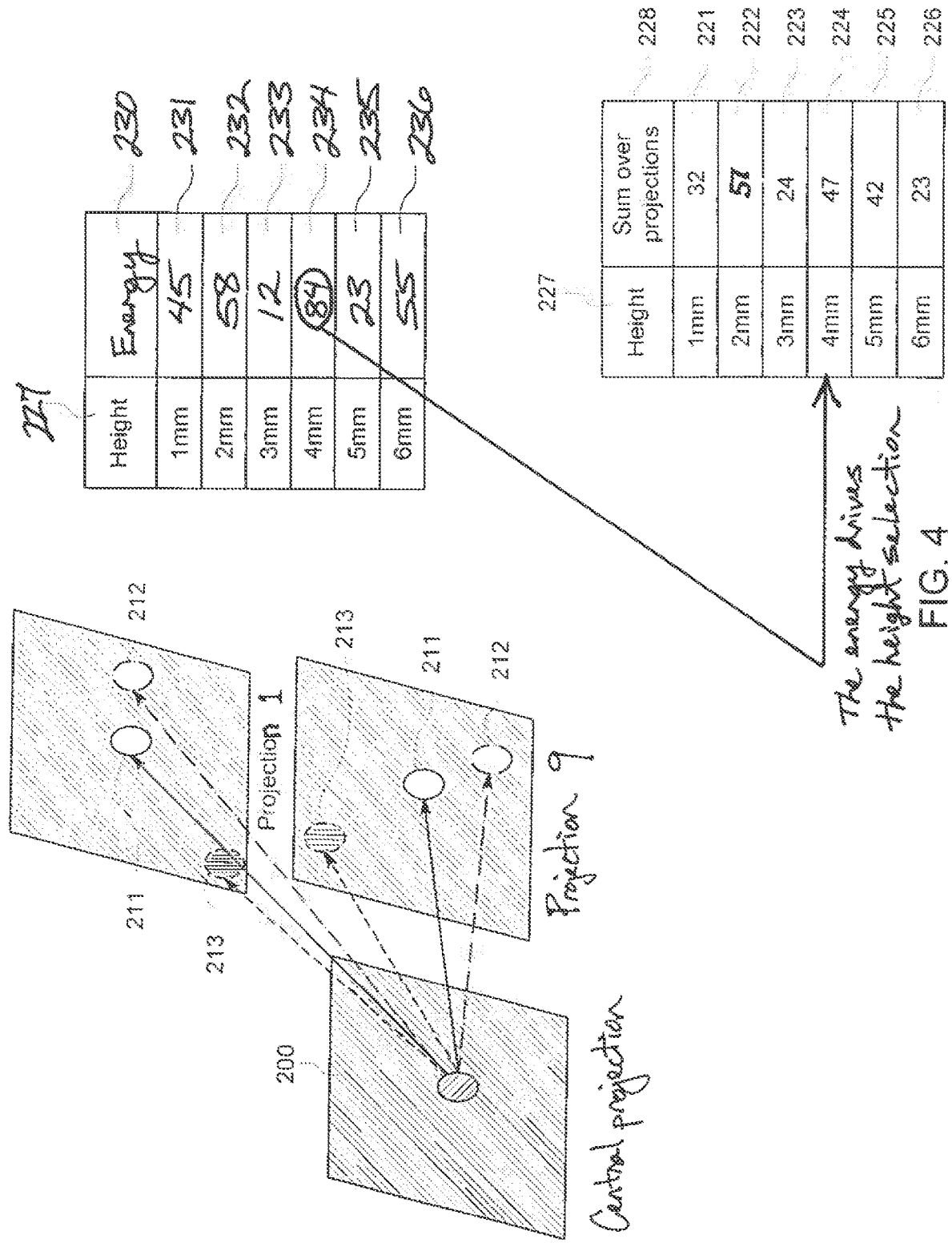
FIG. 4 is a diagrammatic illustration of a method according to another exemplary embodiment of the disclosure.

FIG. 4 is a diagrammatic illustration of a method according to another exemplary embodiment of the disclosure. In this embodiment, the "most likely height" of the 3D object within the breast is selected by ranking an energy value 230 computed for each pixel over all possible heights (231, 232, 233, 234, 235, 236). In a particular embodiment, the energy value can be the square of the accumulated gray level intensity value or the absolute value of the accumulated gray level intensity value. The highest energy value 234 is used to determine the most likely height of the 3D object. Optionally, the energy values may be spatially smoothed across voxels of a given height. The enhanced 2D projection image is then obtained by combining the gray level intensity values of pixel (i, j) with the accumulated gray level intensity values obtained from the most likely height of the 3D object within the breast at pixel (i, j).

The most likely height of each pixel (i, j) is obtained by filtering the acquired 2D tomosynthesis projection images; for each pixel (i, j) of the selected projection image and for a given height, accumulating the filtered gray level intensity values of the corresponding pixel position in at least one of the 2D tomosynthesis projection images; deriving energy values from the accumulated gray level intensity values; optionally spatially smoothing the energy values of a given height; and determining the most likely height for each pixel (i, j) by selecting the maximum energy value among all possible heights.

Figure 5:
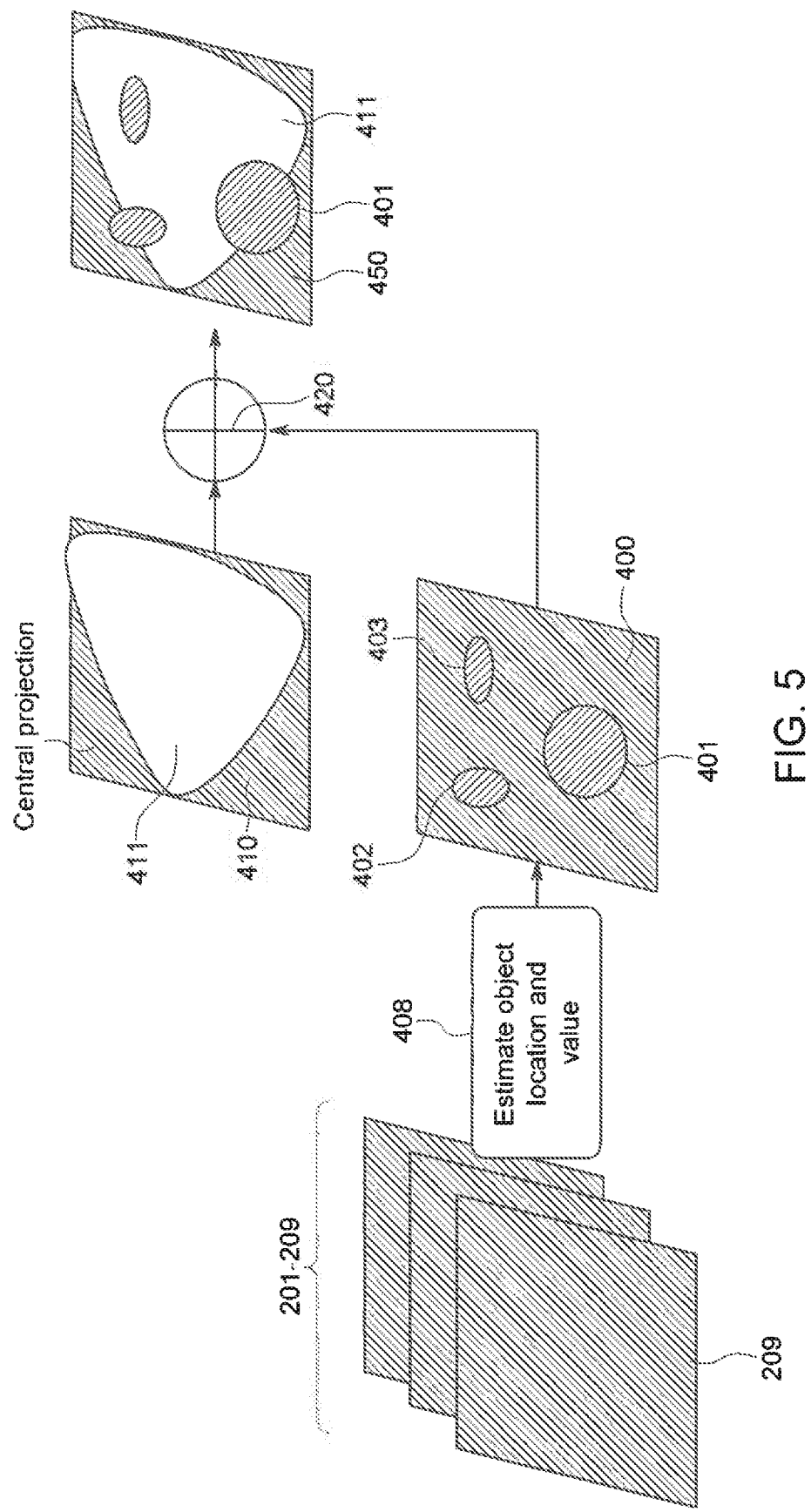
FIG. 5 is a diagrammatic illustration and flow chart of a method according to another exemplary embodiment of the disclosure.

FIG. 5 shows a flow chart of a method according to another exemplary embodiment of the disclosure. The processing of the tomosynthesis projection images (201-209 except the central projection) is performed for different frequency bands corresponding to different 3D object sizes, in order to better render small calcifications, lesions or bigger objects as masses for diagnosis. The location for a given height of a 3D object of a selected projection 410 and corresponding gray level values in the other projections is estimated in step 408 for accumulation, based on the information of the other projections (201-209). Then the determination of the most likely height for each pixel follows by selecting the maximum accumulated gray level intensity value or maximum energy value. The projection 400 provides after the height determination step, the accumulated gray level intensity values of each pixel at the height provided by the most likely height determination step. The projection 400 shows 3D objects of different sizes, whereas the central projection 410 schematically shows image data of breast tissue 411.

In step, 420 the central projection 410 is combined or blended with the projection 400. That is to say the gray level intensity level of pixel (i, j) is combined with the determined accumulated gray level intensity values for each pixel (i, j), to obtain the enhanced 2D projection image 450. The image can be reviewed by a health professional or radiologist, who can analyze 3D objects of interest 401 and underlying tissue 411 for diagnosis.

Figure 6:
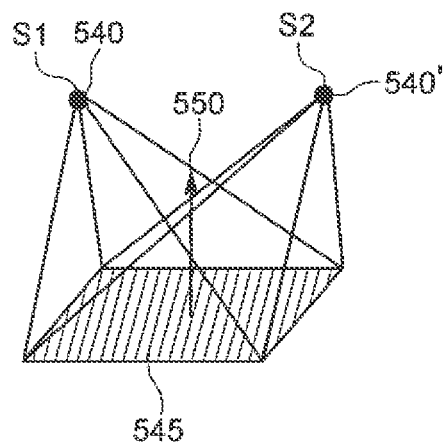
FIG. 6 is a diagrammatic illustration of the acquisition geometry of the imaging system shown in FIG. 1.

FIG. 6 shows a diagrammatic illustration of the acquisition geometry of the imaging system shown in FIG. 1. Specifically, FIG. 6 shows an X-ray source and X-ray detector arrangement. An X-ray detector 545 is fixed in relation to an X-ray source 540. The X-ray source 540 moves during the tomosynthesis acquisition from the source position S1 to the source position S2. Arrow 550 indicates a normal or perpendicular position to the detector plane and is situated in the center of the plane. This normal or perpendicular position 550 points to the source only in the zero projection position. However, all other projections with $\alpha>0$ are not isocentric, thus having the disadvantage that structures within the object of interest may shift from one projection to another.

Figure 7:
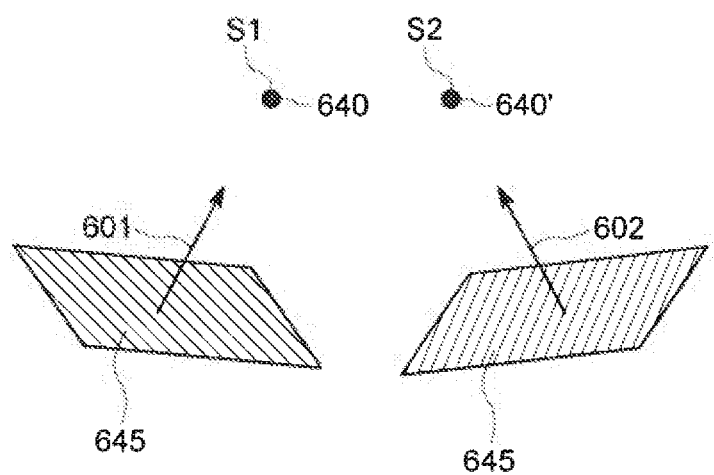
FIG. 7 shows a diagrammatic illustration of the acquisition geometry of the imaging system according to another exemplary embodiment of the disclosure.

FIG. 7 shows a diagrammatic illustration of an acquisition geometry according to another exemplary embodiment of the disclosure. The X-ray source 640 moves as in FIG. 6 from a source position S1 to a source position S2. However, the X-ray detector's central normal or perpendicular positions 601 and 602 point at each position S1 and S2 to the source 640 and 640', respectively. This isocentric geometry can be provided by a virtual rotating X-ray detector. This virtual isocentric X-ray detector allows an improved rendering of a 3D volume image, since the structure within the object of interest shifting from one projection to another is limited.

According to an embodiment of the disclosure each enhanced image projected on an isocentric virtual projection are displayed successively for review. In order to reduce artifacts and noise, the tomosynthesis projection images may further be filtered and/or denoised prior to enhancing or improving the image quality.

This description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:
1. A method for obtaining at least one enhanced image of an object of interest using a system comprising an X-ray source facing an X-ray detector, the method comprising:
   moving the X-ray source to a plurality of positions relative to the X-ray detector, the X-ray detector being stationary, and acquiring a 2D tomosynthesis projection image of the object of interest at each of the plurality of positions;
   enhancing each acquired 2D tomosynthesis projection image;
   projecting each enhanced image on an isocentric virtual X-ray detector to produce a plurality of virtual projections, wherein the normal to the isocentric virtual X-ray detector points towards the X-ray source for each position of the plurality positions to produce a plurality of virtual projections;
   displaying successively the virtual projection images;
   enhancing a selected projection image of the acquired 2D tomosynthesis projection images using at least a subset of the acquired tomosynthesis projection images at a plurality of heights, wherein a most likely height is determined for each pixel (i, j) of the selected projection image, and wherein enhancing the selected projection image comprises:
      for each pixel (i, j) of the selected projection image and for a given height, accumulating gray level intensity values of the corresponding pixel position in at least one of the tomosynthesis projection images;
      ranking the accumulated gray level intensity values for each pixel over all possible heights;

determining the most likely height for each pixel (i, j) by selecting a maximum accumulated gray level intensity value; and combining each pixel's (i, j)'s gray level intensity level with the accumulated gray level intensity value at a height corresponding to the most likely height for pixel (i, j); and displaying an enhanced 2D projection image.

2. The method according to claim 1, wherein the displaying step is performed at an adjustable speed.

3. The method according to claim 1, wherein the accumulating step is performed for different frequency bands obtained by filtering the acquired 2D tomosynthesis projection images.

4. The method according to claim 3, wherein the most likely height of each pixel (i, j) is obtained by: filtering the acquired 2D tomosynthesis projection images;

for each pixel (i, j) of the selected projection image and for a given height, accumulating the filtered gray level intensity values of the corresponding pixel position in at least one of the 2D tomosynthesis projection images;

deriving energy values from the accumulated gray level intensity values;

optionally spatially smoothing the energy values of a given height; and determining the most likely height for each pixel (i, j) by selecting the maximum energy value among all possible heights.

5. The method according to claim 1, wherein the most likely height of each pixel (i, j) is obtained as a combination of maximum accumulated gray level intensity values and 3D marks provided by a computer-aided diagnosis (CAD) system or indicated by a user through a 3D review system.

6. The method according to claim 1, wherein the most likely height of each pixel (i, j) is stored as a height map associated to the enhanced 2D projection image.

7. The method according to claim 1, wherein the selected projection image is the central projection (0°), which is the projection perpendicular to the X-ray detector.

8. The method according to claim 1, wherein at least one 2D tomosynthesis projection image is denoised prior to improving the image quality of at least one of the at least one 2D tomosynthesis projection image.

9. A system for obtaining enhanced images of an object of interest comprising:

an imaging system comprising an X-ray source and an X-ray detector configured to acquire 2D tomosynthesis projection images of the object of interest by moving the X-ray source to a plurality of positions relative to the X-ray detector, wherein a 2D tomosynthesis projection image is acquired at each of the plurality of positions;

a processing unit configured enhance each of the acquired 2D tomosynthesis projection images, and project each enhanced image on an isocentric virtual X-ray detector to produce a plurality of virtual projections, wherein the normal to the isocentric virtual detector points towards the X-ray source for each position of the plurality positions to produce a plurality of virtual projections;

a display configured to successively display the virtual projections;

wherein the processing unit is further configured to compute an enhancement for a selected projection image of the acquired 2D tomosynthesis projection images using at least a subset of the acquired 2D tomosynthesis projection images at a plurality of heights, wherein a most likely height is determined for each pixel (i, j) of the selected projection image, and wherein in computing the enhancement, the processing unit is further configured to:

for each pixel (i, j) of the selected projection image and for a given height, accumulate the gray level intensity values of the corresponding pixel position in at least one of the 2D tomosynthesis projection images;

rank the accumulated gray level intensity values for each pixel over all possible heights;

determine the most likely height for each pixel (i, j) by selecting the maximum accumulated gray level intensity value; and combine pixel (i, j)'s gray level intensity value with the determined maximum gray level intensity values for each pixel (i, j); and the display is configured to display an enhanced projection image.

10. The system according to claim 9, wherein the object of interest is a patient's breast.

11. The system according to claim 9, wherein the most likely height of each pixel (i, j) is obtained as a combination of maximum accumulated gray level intensity value and 3D marks provided by a CAD system or indicated by a user through a 3D review system.

12. The system according to claim 11, wherein the most likely height of each pixel (i, j) is stored as a height map associated to the enhanced 2D projection image.

13. The system according to claim 9, wherein the selected projection image is the central projection (0°), which is the projection perpendicular to the X-ray detector.

14. The system according to claim 9, wherein at least one 2D tomosynthesis projection image is denoised prior to improving the image quality of at least one of the at least one 2D tomosynthesis projection image.

* * * * *